(12) United States Patent
Wang et al.

(10) Patent No.: US 11,147,832 B2
(45) Date of Patent: Oct. 19, 2021

(54) PHARMACEUTICAL COMPOSITION FOR PREVENTION OF RECURRENT URINARY TRACT INFECTION

(71) Applicant: TCM BIOTECH INTERNATIONAL CORP., New Taipei (TW)

(72) Inventors: Ya-Chun Wang, New Taipei (TW); Yu-Ching Chang, New Taipei (TW); Hsiao Tien Ma, New Taipei (TW); Jen-Yau Chen, New Taipei (TW); Yuan-Ju Lee, Taipei (TW); En Meng, Taipei (TW); Shang-Jen Chang, New Taipei (TW)

(73) Assignee: TCM BIOTECH INTERNATIONAL CORP., New Taipei (TW)

( * ) Notice: Subject to any disclaimer, the term of this patent is extended or adjusted under 35 U.S.C. 154(b) by 0 days.

(21) Appl. No.: 16/857,201

(22) Filed: Apr. 24, 2020

(65) Prior Publication Data

US 2020/0338115 A1    Oct. 29, 2020

Related U.S. Application Data

(60) Provisional application No. 62/838,954, filed on Apr. 26, 2019.

(51) Int. Cl.
*A61K 31/737* (2006.01)
*A61P 13/02* (2006.01)
*A61K 9/00* (2006.01)

(52) U.S. Cl.
CPC ............ *A61K 31/737* (2013.01); *A61P 13/02* (2018.01); *A61K 9/0053* (2013.01)

(58) Field of Classification Search
CPC ..... A61K 31/726; A61K 31/737; A61P 13/00; A61P 13/02; A61P 31/04
See application file for complete search history.

(56) References Cited

U.S. PATENT DOCUMENTS

2014/0335134 A1    11/2014    Ko et al.

FOREIGN PATENT DOCUMENTS

| CN | 102370989 A | 3/2012 | |
|---|---|---|---|
| GB | 2486713 A | 6/2012 | |
| JP | 2012116818 A | 6/2012 | |
| WO | 2005072751 A1 | 8/2005 | |
| WO | WO-2005072751 A1 * | 8/2005 | .............. A61P 13/02 |
| WO | 2019124363 A1 | 6/2019 | |

OTHER PUBLICATIONS

Jose Antonio Ortega Martell, et al. "Prevention of recurrent urinary tract infections: bridging the gap between clinical practice and guidelines in Latin America." Therapeutics Advances in Urology. Mar. 31, 2019 (Mar. 31, 2019), vol. 11; pp. 29-40.

Tseng, Chi-Shin, et al. "The efficacy of pentosan polysulfate monotherapy for preventing recurrent urinary tract infections in women: A multicenter open-label randomized controlled trial." Journal of the Formosan Medical Association. Dec. 5, 2019 (Dec. 5, 2019); pp. 1-6.

C L Parsons, "A model for the function of glycosaminoglycans in the urinary tract", World J Urol. 1994;12(1):38-42. doi: 10.1007/BF00182049. the whole document; especially the abstract, p. 39-41; paragraphs for Bacterial adherence, Altered epithelial permeability and disease.

* cited by examiner

*Primary Examiner* — Leigh C Maier
(74) *Attorney, Agent, or Firm* — ScienBiziP, P.C.

(57) ABSTRACT

The present disclosure provides a use of pentosan polysulfate sodium (PPS) in the manufacture of a medicament for the prevention of recurrent urinary tract infection (rUTI) in a human subject, comprising a therapeutically effective dosage for oral administration of PPS, wherein the therapeutically effective dosage for oral administration of PPS is 5-1 mg/kg/day.

5 Claims, 12 Drawing Sheets

PHARMACEUTICAL COMPOSITION FOR PREVENTION OF RECURRENT URINARY TRACT INFECTION

CROSS-REFERENCE TO RELATED APPLICATION

The application claims the benefit of U.S. provisional patent application No. 62/838,954, filed on Apr. 26, 2019, the entirety of which is incorporated herein by reference.

FIELD OF THE DISCLOSURE

The present disclosure relates to a pharmaceutical composition for the prevention of a recurrent urinary tract infection.

BACKGROUND OF THE DISCLOSURE

Lower urinary tract infection is caused by uropathogenic bacteria replacing the normal flora of the lower urinary tract, and is a common infectious disease among women. After a complete clinical resolution, typically with antibiotic treatments, about 20% to 30% of women who previously experienced a lower urinary tract infection might suffer from a recurrence of urinary tract infection within a year. This is defined as a recurrent urinary tract infection (rUTI). The uropathogenic bacteria in rUTI are originated from extraurinary tissues or persisted in underlying epithelium of bladder.

Currently, preventive measures for rUTI may include antibiotic and non-antibiotic prophylaxes. Long-term administration of low dose antibiotic has been proven to be effectively prevent rUTI. However, the uropathogenic bacteria in the lower urinary tract of the patient may develop drug resistance after the administration of low dose antibiotics. Non-antibiotic prophylaxis may include intravesical instillation with hyaluronic acid, vaginal instillation with estrogen, and supplementations of cranberries, vitamin C, or D-mannose.

Among the non-antibiotic prophylaxes listed above, the only clinically proven preventive measure for rUTI is the intravesical instillation with hyaluronic acid. However, the intravesical instillation is a complicated procedure that can only be performed by the physician.

Therefore, it is an objective of the present disclosure to provide a reliable and convenient preventive measure for rUTI.

BRIEF SUMMARY OF THE DISCLOSURE

An objective of the present disclosure is to provide a therapeutically effective dosage of a pharmaceutical composition, for the prevention of recurrent urinary tract infection (rUTI).

An objective of the present disclosure is to provide a therapeutically effective dosage for the orally-administered pentosan polysulfate sodium (PPS), for the prevention of rUTI.

An objective of the present disclosure is to provide a use of PPS in the manufacture of a medicament for the prevention of rUTI, comprising the therapeutically effective dosage for oral administration of PPS.

The present disclosure provides a use of PPS in the manufacture of a medicament for the prevention of rUTI in a human subject, comprising a therapeutically effective dosage for oral administration of PPS, wherein the therapeutically effective dosage for oral administration of PPS is 5-1 mg/kg/day.

According to an embodiment of the present disclosure, the therapeutically effective dosage for oral administration of PPS is 3.4-1.67 mg/kg/day in the human subject.

According to an embodiment of the present disclosure, the therapeutically effective dosage for oral administration of PPS is 1.67-1 mg/kg/day in the human subject.

According to an embodiment of the present disclosure, the therapeutically effective dosage for oral administration of PPS is 1.42-1.25 mg/kg/day in the human subject.

According to an embodiment the present disclosure, the therapeutically effective dosage for oral administration of PPS is 1.25-1 mg/kg/day in the human subject.

The present disclosure provides a method for preventing rUTI in the human subject, comprising a step of: orally administering the human subject a therapeutically effective dosage of PPS, wherein the therapeutically effective dosage is 5-1 mg/kg/day in the human subject.

BRIEF DESCRIPTION OF THE DRAWINGS

The accompanying drawings illustrate one or more embodiments of the present disclosure and, together with the written description, explain the principles of the present disclosure. Wherever possible, the same reference numbers are used throughout the drawings to refer to the same or like elements of an embodiment.

In accordance with common practice, the various described features are not drawn to scale and are drawn to emphasize features relevant to the present disclosure. Like reference characters denote like elements throughout the figures and text.

DETAILED DESCRIPTION OF THE PREFERRED EMBODIMENTS

Figure 1:
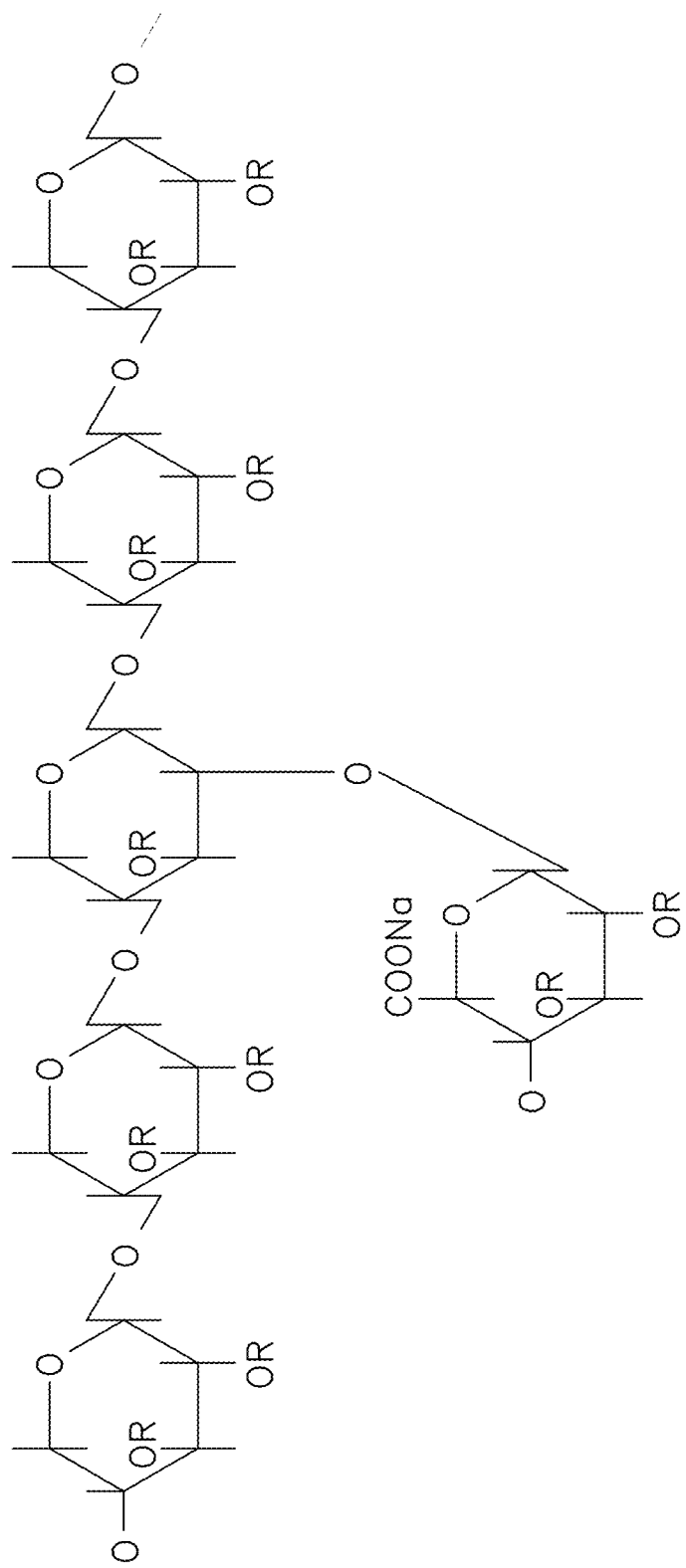
FIG. 1 is a chemical structure of pentosan polysulfate sodium (PPS), in accordance with an embodiment of the present disclosure.

The present disclosure will now be described more fully hereinafter with reference to the accompanying drawings illustrating various embodiments of the disclosure. The present disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the terms "and/or" and "at least one" include any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

As used herein, the terms "pentosan polysulfate sodium" (PPS) refers to a semi-synthetic, heparin-like carbohydrate-derived macromolecule with a molecular weight of 4000-6000 Dalton. PPS is a white, odorless powder being slightly hygroscopic, and has a solubility of up to 50% at pH 6 in water. FIG. 1 is a chemical structure of PPS, in accordance with an embodiment of the present disclosure. The chemical formula of PPS is $(C_5H_6Na_2O_{10}S_2)_n$, and R in FIG. 1 is $SO_3Na$. The PPS is also the active pharmaceutical ingredient (API) of a commercially available drug, Urosan®.

The administration of PPS has been approved as a treatment for internal cystitis (IC) or painful bladder syndrome (PBS), because the chemical structure and property of PPS is similar to a glycosaminoglycan layer on the bladder wall. The glycosaminoglycan layer on the bladder wall includes hyaluronic acid, chondroitin sulfate, keratan sulfate, and heparin sulfate. The glycosaminoglycans on the bladder wall is a protective layer for epidermal cells, and prevents the attachment of uropathogenic bacteria onto the bladder wall, thus prevents further bacterial infection of the bladder. PPS is structurally similar to heparin sulfate, which is a member of the glycosaminoglycans and an anti-coagulant. Due to its' similarity with the glycosaminoglycans, PPS serves as a protective coating of the bladder wall when excreted in urine, preventing the attachment of uropathogenic bacteria onto the bladder wall. Several commonly reported adverse effects of PPS includes: nausea, diarrhea, indigestion, headache, rash, dyspepsia, abdominal pain, liver function abnormalities, dizziness, and rectal hemorrhage.

As used therein, the term "preventing" or "prevention" encompasses disease preventive measures prior to the exposure of pathogens or prior to an onset of one or more symptoms of the disorder or disease on the subject. Prevention methods provided herein includes an oral administration to a subject an effective amount of PPS for a designated time period. Suitable subjects include human subjects who are susceptible to a disease identified herein, or animal models that prior to the exposure of a particular pathogen of the disease identified herein.

As used herein, "therapeutically effective dosage" refers to an amount effective, at dosages and for periods of time necessary, to achieve the desired therapeutic result, such as suppression or prevention of bacterial infection within a designated tissue or organ. A therapeutically effective dosage of PPS may vary according to factors such as age, gender, body weight, and/or body surface area of the subject. A therapeutically effective dosage is also one in which any toxic or detrimental effects of PPS are outweighed by the therapeutically beneficial effects.

The present disclosure provides a method of preventing recurrent urinary tract infection (rUTI) by orally administrating the therapeutically effective dosage of PPS, in accordance with an embodiment of the present disclosure. For patients suffering from rUTI, the bladder mucosa is damaged in every UTI episodes, thus increases the susceptibility of a next bacterial infection. When being excreted in urine, PPS serves as a protective coating to epidermal cells of the urinary tract. The protective coating provided by the PPS restores the urothelial mucosa, thus inhibits the attachment and invasion of the uropathogenic bacteria to the urinary tract, and also facilitates the recovery of a damaged bladder epithelium. Therefore, recurrent infections in the urinary tract caused by the uropathogenic bacteria can be prevented.

The present disclosure also provides a use of PPS in the manufacture of a medicament for the prevention or rUTI, comprising the therapeutically effective dosage for oral administration, in accordance with an embodiment of the present disclosure.

The following experiments demonstrates the efficacy of orally administered PPS and the therapeutic effective dosages of orally administered PPS for preventing rUTI, in rats or in human subjects, in accordance with an embodiment of the present disclosure.

Example 1: The Efficacy of Orally Administered PPS in Preventing Urinary Tract Infections (UTI) Induced by Uropathogenic *Escherichia coli* in the Rats The purpose of the current example is to establish a rat UTI model, investigate effects of orally-administered intravesical PPS in the rat UTI model, clarify biomarkers related to UTI, and to develop new targets for the prevention of UTI.

The current example treats Sprague-Dawley (SD) rats with uropathogenic *Escherichia coli* (UPEC) to establish the rat UTI model. UPEC is known as the primary cause of UTI. Virulence factors of UPEC can mediate its' adhesion and invasion toward bladder epithelial cells, and flagella of UPEC allows it to escape from immune reactions from the host. The UPEC used in the current example is ATCC®700336™, designation: J96 (serotype O4:K6), purchased from Food Industry Research and Development Institute of Taiwan. The UPEC is stored in trypticase soy agar/broth, and is centrifuged at 5,000 rpm for 10 minutes. Pellets of the UPEC after the centrifugation are dissolved in 10 mL sterile phosphate buffered saline (PBS). The cell density of the UPEC is adjusted to an optical density (OD600) of 1 to 1.1. This optical density is corresponded to the cell density of $8 \times 10^7$ to $2 \times 10^8$ colony forming units (CFU)/mL. The UPEC is then made into a 250 μL 0.9% N/S solution of $8 \times 10^7$ CFU for treating the rats.

30 healthy female SD rats are randomly divided into three groups: a control group, an UTI model group, and a PPS prevention group, whereby each of the above groups has 10 female SD rats. The UTI model group is denoted as "UTI" and the PPS prevention group is denoted as "UROpre" in FIGS. 3-7.

Figure 2:
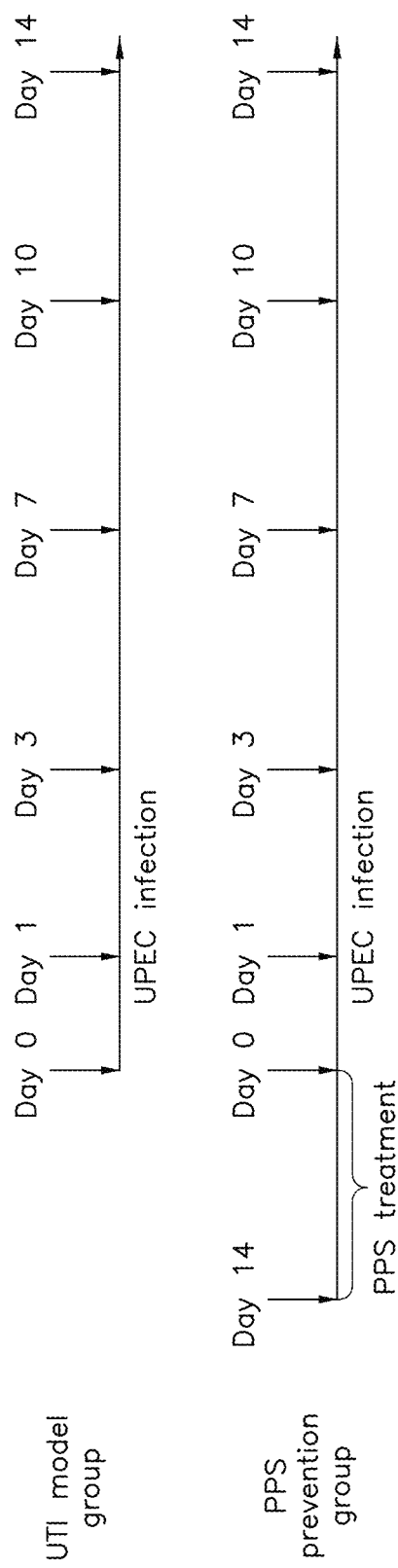
FIG. 2 is an experiment flow chart of PPS oral administration experiments in rats, in accordance with an embodiment of the present disclosure.

FIG. 2 is an experimental flow chart of the current example, in accordance with an embodiment of the present disclosure. The control group did not receive any treatment of PPS or the UPEC. The UTI model group and the PPS prevention group are infected with the UPEC by trans-urethral catherization on Day 1. The PPS prevention group is treated with the PPS by oral gavage with a 18G stainless-steel gavage needle attached to a 3 mL tuberculin syringe from Day −14 to Day 0. The PPS dosage for the rats in the current example is 30 mg/kg/day. Urine samples of the rats are collected by trans-urethral instillation by PESO catheter on Day 1, 3, 7, 10, and 14, and blood samples are also collected on Day 1, 3, 7, 10, and 14 from the tail vein using 23G needles with 1 mL syringe. The rats are sacrificed at Day 14. 50 μL of the urine samples are diluted 10 folds in LB broths, and undiluted urine samples are spotted in triplicate on LB agar plates. The LB broths and the LB agar plates are incubated at 37° C. for 16 to 18 hours. The UPEC in the LB broths and on the LB agar plates are quantified after the incubation. The urinary tract tissues are obtained from kidney and bladder after the rats are sacrificed, and H/E staining is conducted to examine histology of the urinary tract tissues.

Figure 3:
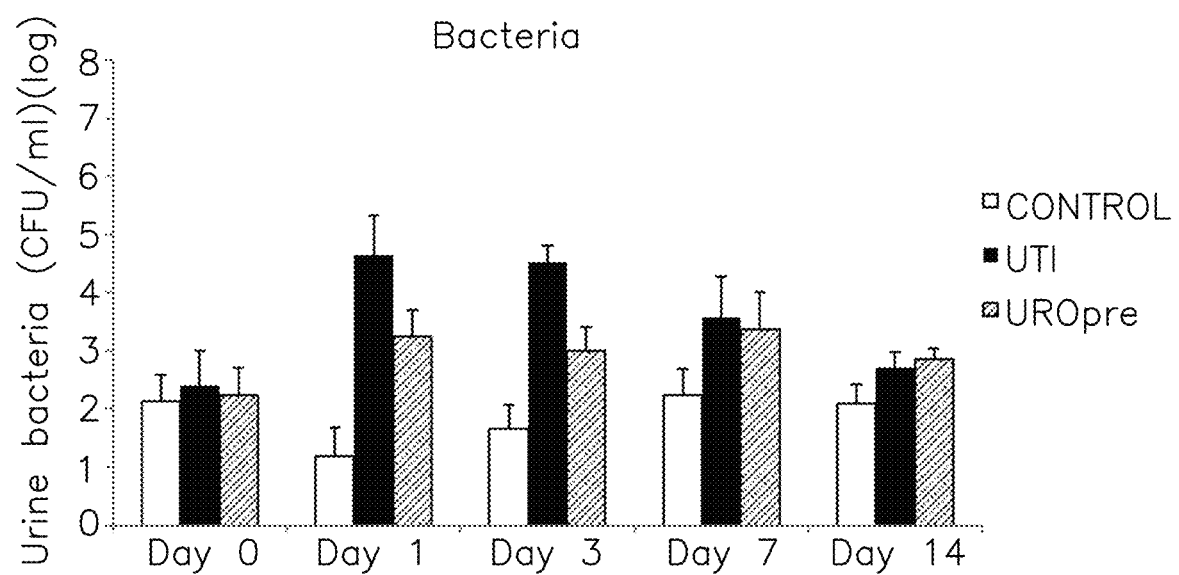
FIG. 3 is a bar chart comparing the urine bacterial counts of a control group, a UTI model group, and a PPS prevention group, in the PPS oral administration experiment in the rats, in accordance with an embodiment of the present disclosure.

FIG. 3 is a bar chart comparing urine bacterial counts of the control group, the UTI model group, and the PPS prevention group, in accordance with an embodiment of the present disclosure. FIG. 3 shows that the urine bacterial counts of the control group, the UTI model group, and the PPS prevention group are below $10^3$ CFU/mL on Day 0, and the urine bacterial counts in the control group have remained below $10^3$ CFU/mL in the current example. The urine bacterial counts in the PPS prevention group have been lower than the urine bacterial counts in the UTI model group on Day 1, Day 3, and Day 7, this suggests PPS may lead to an early inhibition of the UPEC growth in the current example.

Figure 4:
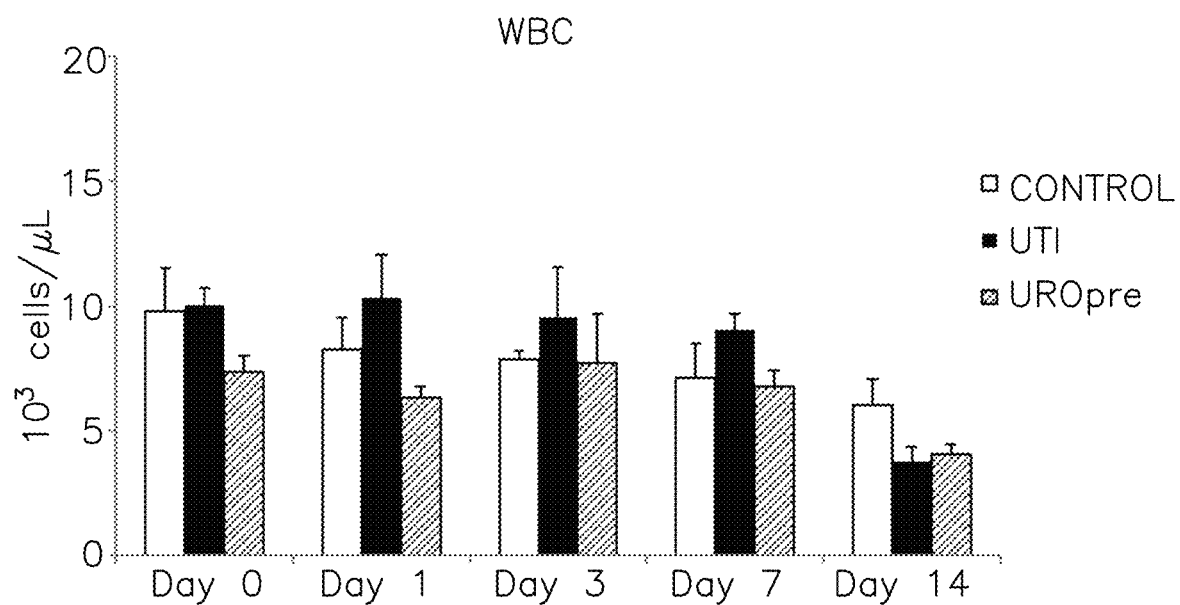
FIG. 4 is a bar chart comparing peripheral white blood cell (WBC) counts of the control group, the UTI model group, and the PPS prevention group, in the PPS oral administration experiment in the rats, in accordance with an embodiment of the present disclosure.

FIG. 4 is a bar chart comparing peripheral white blood cell (WBC) counts in the control group, the UTI model group, and the PPS prevention group, in accordance with an embodiment of the present disclosure. The WBC counts in different groups reflect conditions of the UPEC infection in the rats: a higher WBC count may represent a more severe UPEC infection. The WBC counts of the PPS prevention group are in steady decline after Day 3, and are fewer than the WBC counts in the UTI model group on Day 1, Day 3, and Day 7. The WBC counts in the UTI model group have remained as the highest among 3 groups on Day 1, Day 3, and Day 7.

Figure 5:
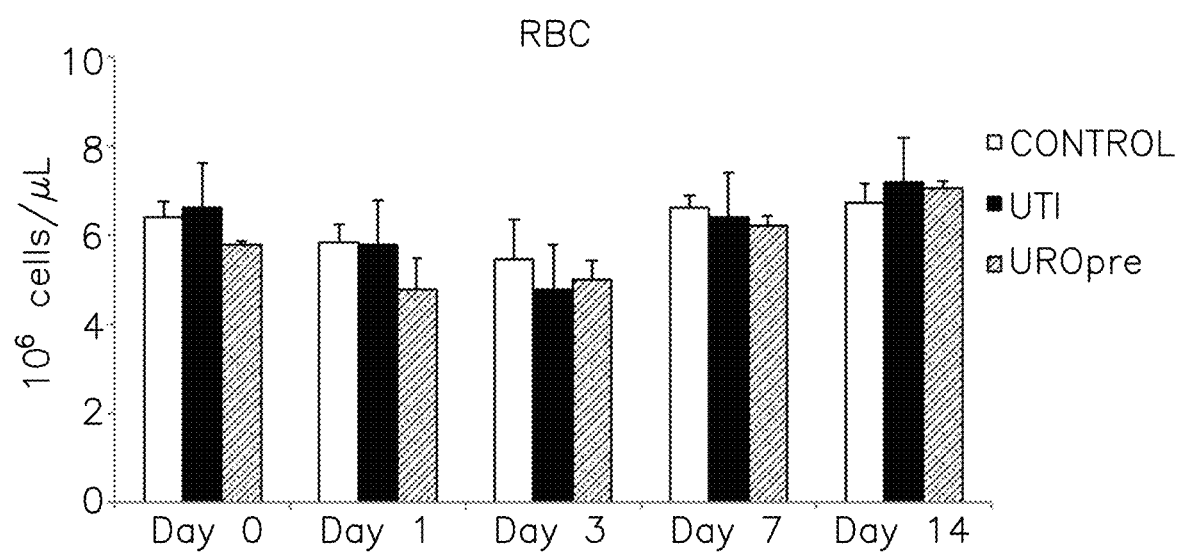
FIG. 5 is a bar chart comparing peripheral red blood cell (RBC) counts of the control group, the UTI model group, and the PPS prevention group, in the PPS oral administration experiment in the rats, in accordance with an embodiment of the present disclosure.

FIG. 5 is a bar chart comparing peripheral red blood cell (RBC) counts in the control group, the UTI model group, and the PPS prevention group, in accordance with an embodiment of the present disclosure. There is no significant differences among the RBC counts in different groups of rats in the current example.

Figure 6:
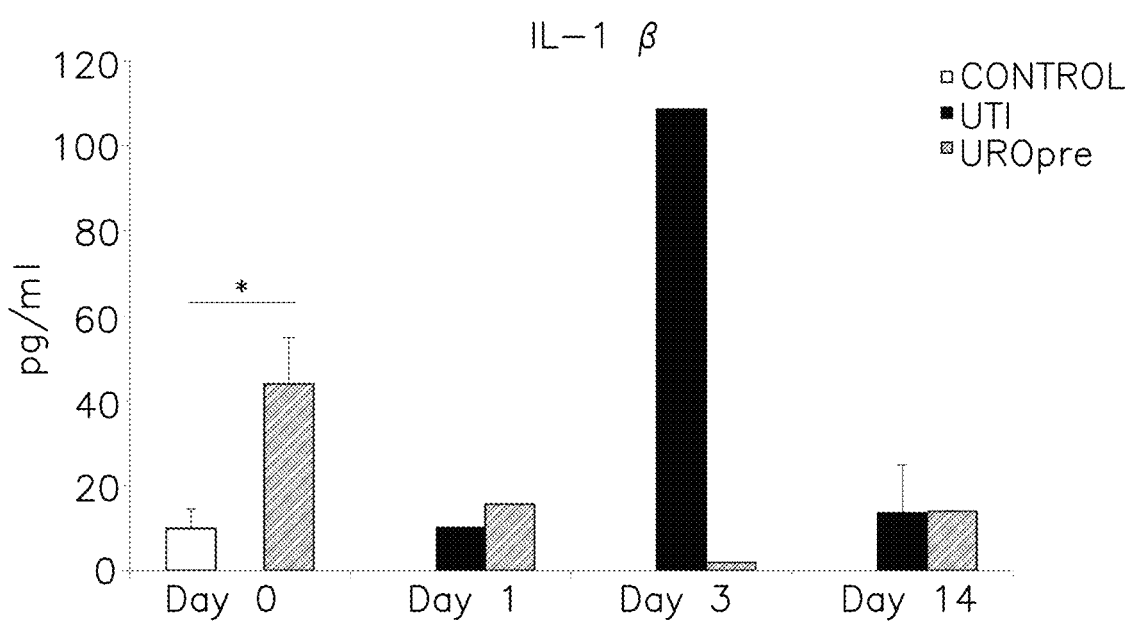
FIG. 6 is a bar chart comparing peripheral IL-1β levels in the control group, the UTI model group, and the PPS prevention group, in the PPS oral administration experiment in the rats, in accordance with an embodiment of the present disclosure.
Figure 7:
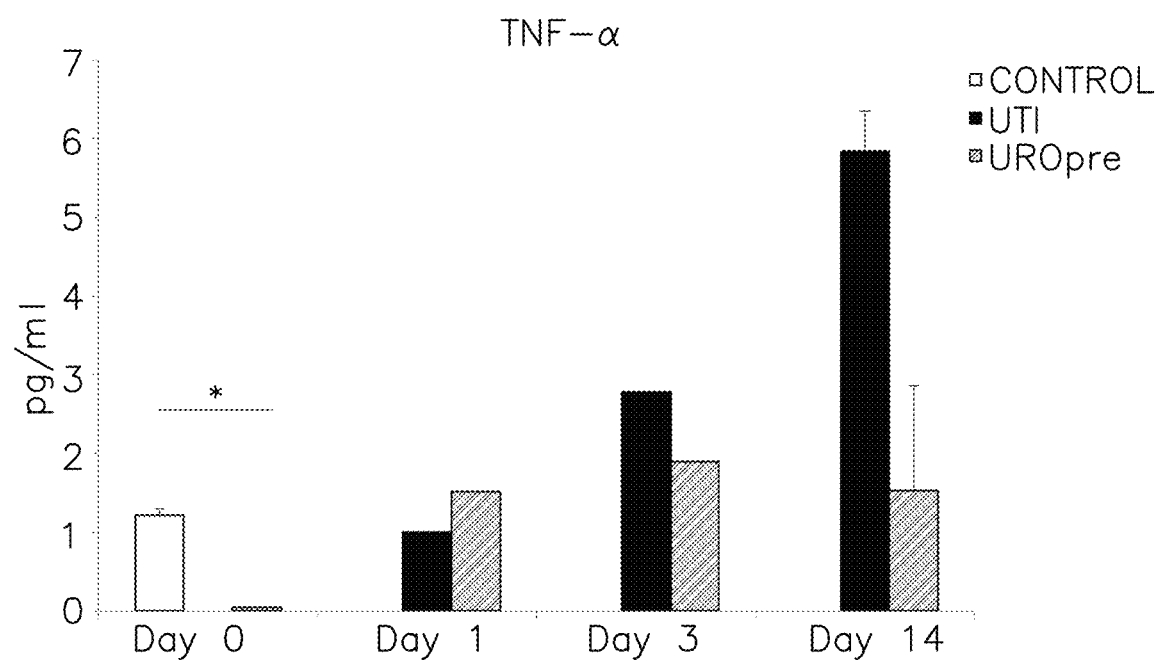
FIG. 7 is a bar chart comparing peripheral TNF-α levels in the control group, the UTI model group, and the PPS prevention group, in the PPS oral administration experiment in the rats, in accordance with an embodiment of the present disclosure.

Luminex assays are used to evaluate peripheral blood biomarkers relevant to infection or inflammation. FIG. 6 is a bar chart comparing the Luminex assay results for IL-1β in the control group, the UTI model group, and the PPS prevention group, in accordance with an embodiment of the present disclosure. IL-1β level is relevant to a current inflammation or infection, and a higher IL-1β level indicates a more severe inflammation. The IL-1β level on Day 3 in the PPS prevention group is significantly lower than the UTI model group. This shows the infections caused by the UPEC in the PPS prevention group are in better control than the infection in the UTI model group. FIG. 7 is a bar chart comparing the Luminex assay results for TNF-α in the control group, the UTI model group, and the PPS prevention group, in accordance with an embodiment of the present disclosure. TNF-α is a cytokine that promotes inflammatory responses, and a higher TNF-α level indicates a more severe inflammation in the rats. The PPS prevention group exhibits lower TNF-α levels than the UTI model group in Day 3 and Day 14, indicating weaker inflammatory responses.

Figure 8A:
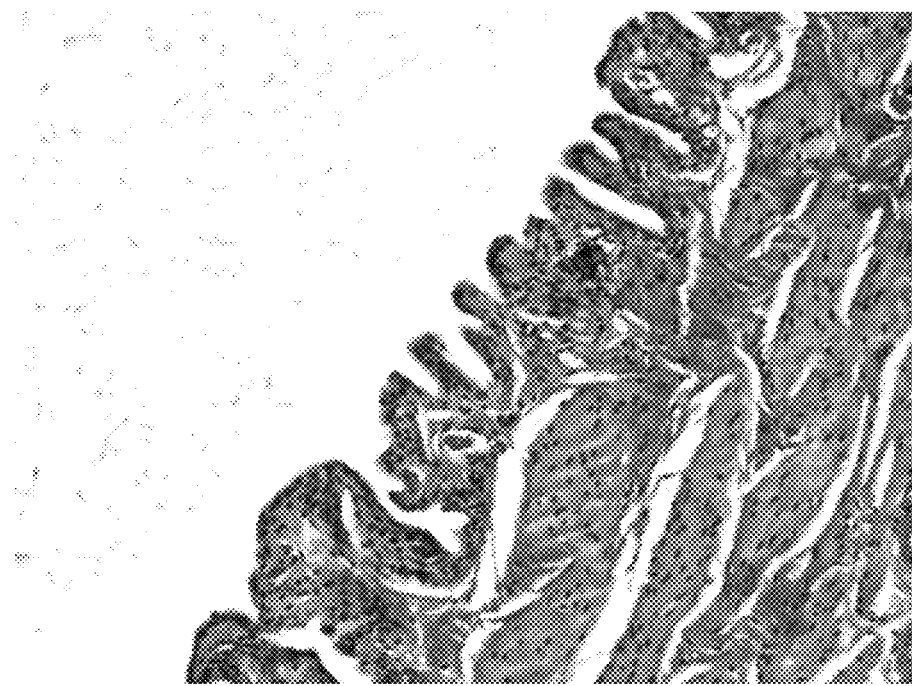
FIG. 8A-8C are H/E staining results of bladders in the control group, the UTI model group, and the PPS prevention group, in the PPS oral administration experiment in the rats, in accordance with an embodiment of the present disclosure.
Figure 8B:
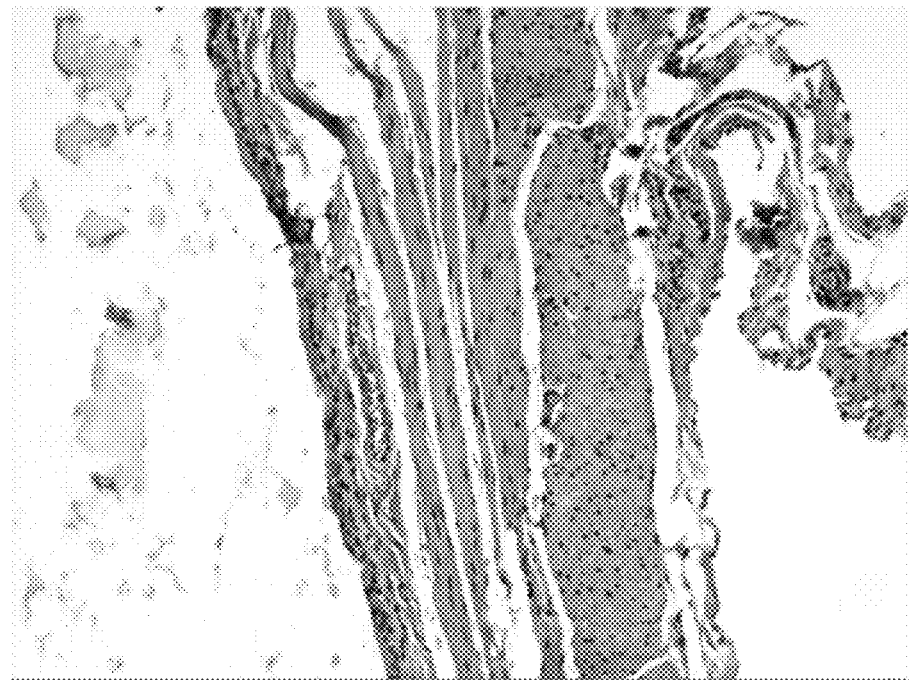
Figure 8C:
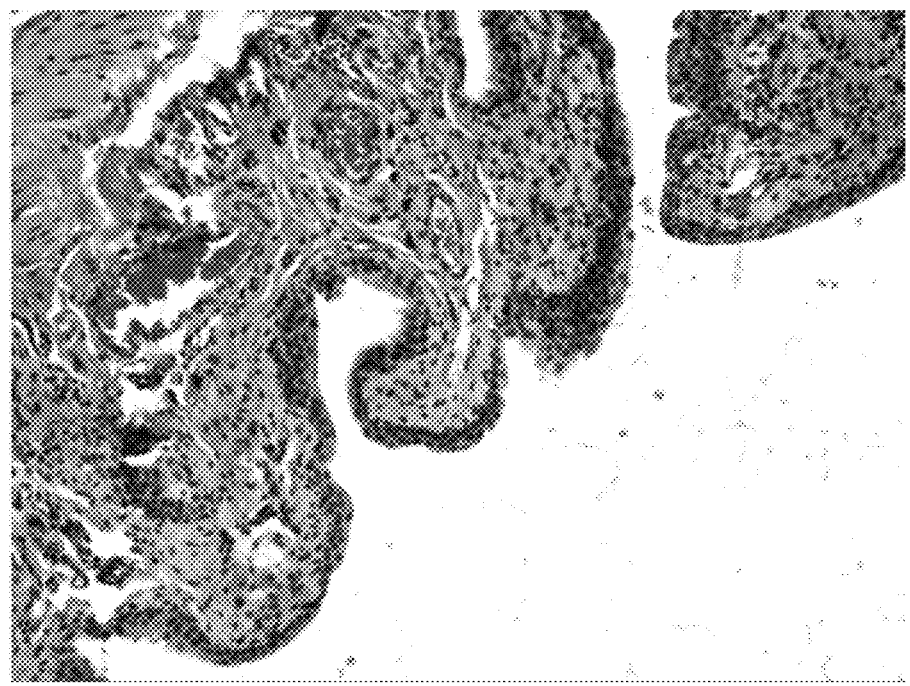

FIG. 8A is a H/E staining result of a bladder tissue in the control group; FIG. 8B is a H/E staining result of a bladder tissue in the UTI model group; FIG. 8C is a H/E staining result of a bladder tissue in the PPS prevention group, in accordance with an embodiment of the present disclosure. A fresh layer of accumulated epithelial cells can be observed in FIG. 8C. The freshly accumulated epithelial cells on a peripheral of the bladder epithelium in FIG. 8C demonstrate that the protective effects of PPS coating also lead to a more robust bladder epithelium, which is known to be crucial for developing resistance to the UPEC infection.

To conclude, the PPS oral administration of 30 mg/kg/day for 14 days for the rats in the current example effectively reduces UTI in the rats, and results in lower levels of inflammatory-related cytokines when comparing with the UTI model group.

Example 2: The Efficacy of Orally Administered PPS in Preventing Recurrent Urinary Tract Infection in the Human Subjects The current example is a multicenter, prospective, open-label, phase II, randomized controlled trial. The purpose of the current example is to investigate the effects of orally administered PPS in the prevention of rUTI in the human subjects. The study period of the current trial is 16 weeks, which is expected to cover most of the rUTI episodes.

The human subjects in the current example are screened and recruited in the OPD. Eligible patients are 20-70 year-old female patients with confirmed UTI ≥2 times in the past 6 months, or ≥3 times in the past 12 months, and had prior antibiotics treatment for previous UTI episodes(s). The eligible patients are without lower urinary tract symptoms and completely recovered from the last UTI episode.

Patients with the following criteria are also excluded: allergic reaction to PPS, undergoing surgery within 24 week in a follow-up period of the current trial, participating in any intervention study 90 days before screening, bladder instillation with hyaluronic acid within 3 months before screening, pregnancy, breast feeding, upper urinary tract infection, fever>38° C., serum WBC count greater than 12,000/mm$^3$, urinary catheterization within 1 week, urinary tract anomalies, interstitial cystitis, urolithiasis, renal insufficiency, cancer history, immunocompromised, organ transplant history, pelvic organ prolapse stage II or higher, post-voiding residual urine more than 100 ml, stress or urge urinary incontinence, and positive urine culture during screening. 45 patients are screened for eligibility, with only 27 patients remained and 18 patients are excluded. The screening in the current trial is defined as Visit 1.

The 27 patients remained are randomized to a PPS group (N=13) and a control group (N=14). The PPS are orally administered to the PPS group according to a continuous daily dosing regimen of 100 mg, 3 times a day for the first 8 weeks (total administered amount is 300 mg PPS per day). Then, the dosing regimen is changed to 100 mg 2 times a day for the remaining 8 weeks (total administered amount is 200 mg PPS per day). The PPS can be taken either 1 hour before or 2 hours after meal. Any forms of UTI prophylaxis or treatment, including antibiotics, hyaluronic acid instillation, cranberry, nonsteroidal anti-inflammatory drugs, or steroids, are forbidden in the study period of the current trial. One patient in the PPS group has dropped out of the current trial immediately after randomization without receiving any PPS administration. The control group does not receive any placebo administration. The patients in both groups are visited every four week from the 0$^{th}$ week (Visit 2), the 4$^{th}$ week (Visit 3), the 8$^{th}$ week (Visit 4), the 12$^{th}$ week (Visit 5), to the 16$^{th}$ week (Visit 6), and Visit 6 is marked as the end of the current trial.

The patients are required to report relevant urinary tract symptoms to an investigator, during each of the visits. A diagnosis of UTI was made on the basis of patient-reported symptoms (dysuria, urinary frequency and urge, suprapublic pain, nocturia, or hematuria) and urine analysis (WBC>5 per HPF, nitrite positive, or leukocyte esterase positive). An urine culture is conducted for the patients who met only one of the symptoms above and with a positive urine analysis, to confirm the diagnosis of the UTI. Additional urine cultures are obtained for patients without UTI recurrence on the 16$^{th}$ week (Visit 6, end of the current trial). Information regarding adverse events, including grade of severity (according to National Cancer Institute Common Terminology Criteria for Adverse Events, version 5.0), timing, and their relationship with the medication assessed by the investigator, are also recorded at each of the visits. Due to the weak anticoagulant effects of the PPS, complete blood counts, liver function tests, prothrombin time/international normalized ratio (PT/INR), and activated partial thromboplastin time (aPTT) are performed at Visit 1, Visit 4, and Visit 6.

For analyzing results of the current study, all statistical analyses are performed using MedCalc Statistical Software version 19.0.3. The Mann-Whitney U test and Student's t-test are used to compare medians and means, respectively. Contingency tables are constructed for comparisons using a chi-square test and Fisher's exact test. The Kaplan—Meier method is used for the construction of survival curves. A log-rank test and Cox proportional hazard model are used to compare recurrence-free survival duration between groups. All tests are 2-tailed. A P-value<0.05 is considered significant.

A primary endpoint for the current trial is UTI recurrence-free survival. In the current trial, none of the patients in the PPS group had lower urinary tract symptoms nor positive urine analysis, and thus none of the patients in the PPS group had UTI recurrences. In contrast, 9 out of 14 patients (about 64%) in the control group had UTI recurrent recurrences. Table 1 provides demographic descriptions and the UTI recurrence results of the patients enrolled in the current trial.

TABLE 1

Demographic characteristics and the UTI recurrence results of the patients in the current trial

| | Treatment group | | | | | | |
|---|---|---|---|---|---|---|---|
| | Control group (N = 14) | | | PPS group (N = 12) | | | p-value |
| | Mean | Median | SD | Mean | Median | SD | |
| Age (year) | 57.7 | 57.6 | 8.54 | 51.1 | 48.2 | 8.9 | 0.067 |
| Serum creatinine (mg/dL) | 0.63 | 0.6 | 0.07 | 0.71 | 0.7 | 0.13 | 0.062 |
| UTI times before screening | 5.7 | 4 | 3.6 | 5.4 | 5 | 2.5 | 0.71 |
| | Number | % | | Number | % | | |
| Diabetes mellitus | 0 | 0 | — | 0 | 0 | — | — |
| Menopause | 8 | 57.1% | — | 41.7% | 0 | — | 0.44 |
| UTI recurrence | 9 | 64.3% | — | 0 | 0 | — | <0.001 |

According to previous studies, commonly adverse effects of orally administered PPS includes nausea (1.4%-7.9%), diarrhea (1-14.9%), headache (1-2.9%), rash (3%), dyspepsia (2%), abdominal pain (2%), liver function abnormalities (1-2%), dizziness (1%), and rectal hemorrhage (4%). However, none of the above adverse effects are observed in the PPS group of the current trial. The complete blood counts, the liver function tests, and coagulant-related tests reveal no abnormalities in all of the patients.

Figure 9:
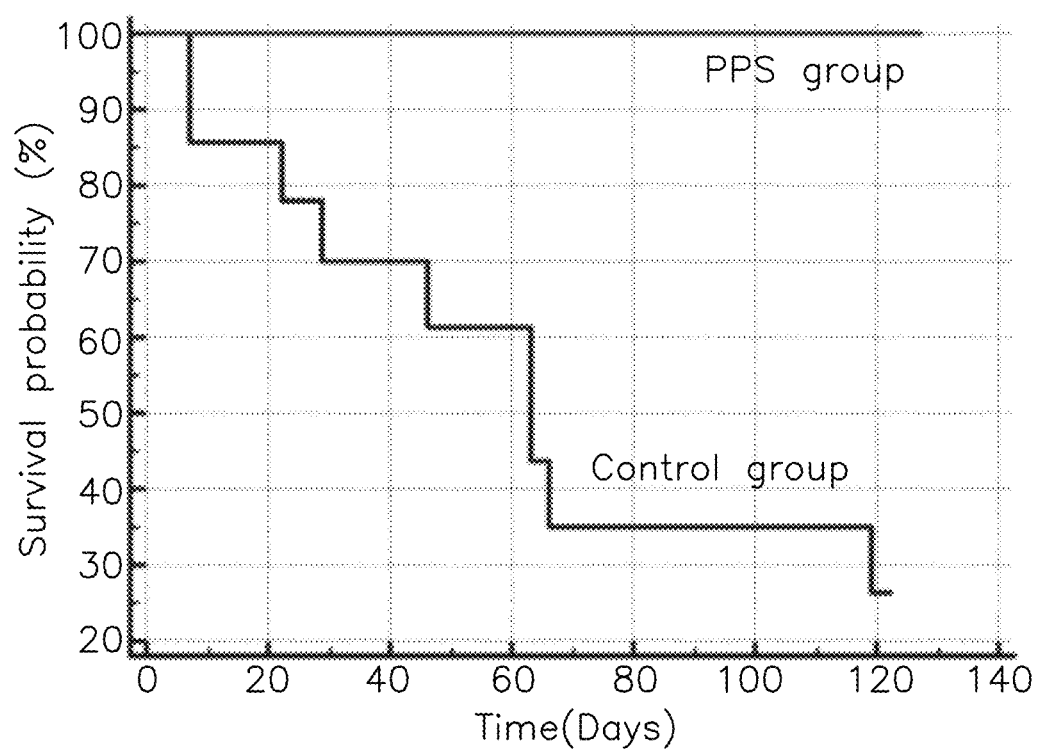
FIG. 9 is a Kaplan-Meier survival curve for a PPS oral administration trial in human subjects, in accordance with an embodiment of the present disclosure.

FIG. 9 is a Kaplan-Meier survival curve for UTI recurrence-free survival in 26 patients in the control group and the PPS group, in accordance with an embodiment of the present disclosure. It can be concluded from FIG. 9 that the overall UTI recurrence free survival is significantly higher in the PPS group than in the control group (log-rank test p=0.0004). A higher than expected clinical benefit in the PPS group during the study period has led to an early termination of further patient enrollment. According to the current trial, the oral administration of PPS has proven to achieve excellent protective effect in preventing rUTI in the human subjects.

Figure 10:
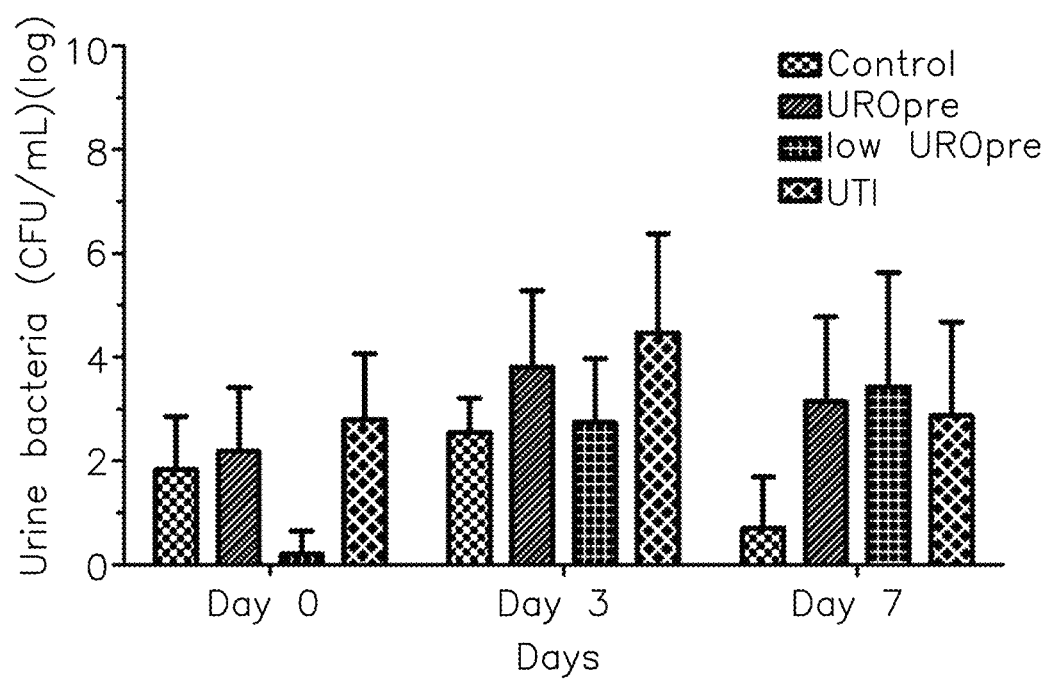
FIG. 10 is a bar chart comparing urine bacterial counts of a control group, a normal PPS dosage group, a reduced PPS dosage group, and a UTI model group in a PPS oral dosage administration experiment in the rats, in accordance with an embodiment of the present disclosure.
Figure 11:
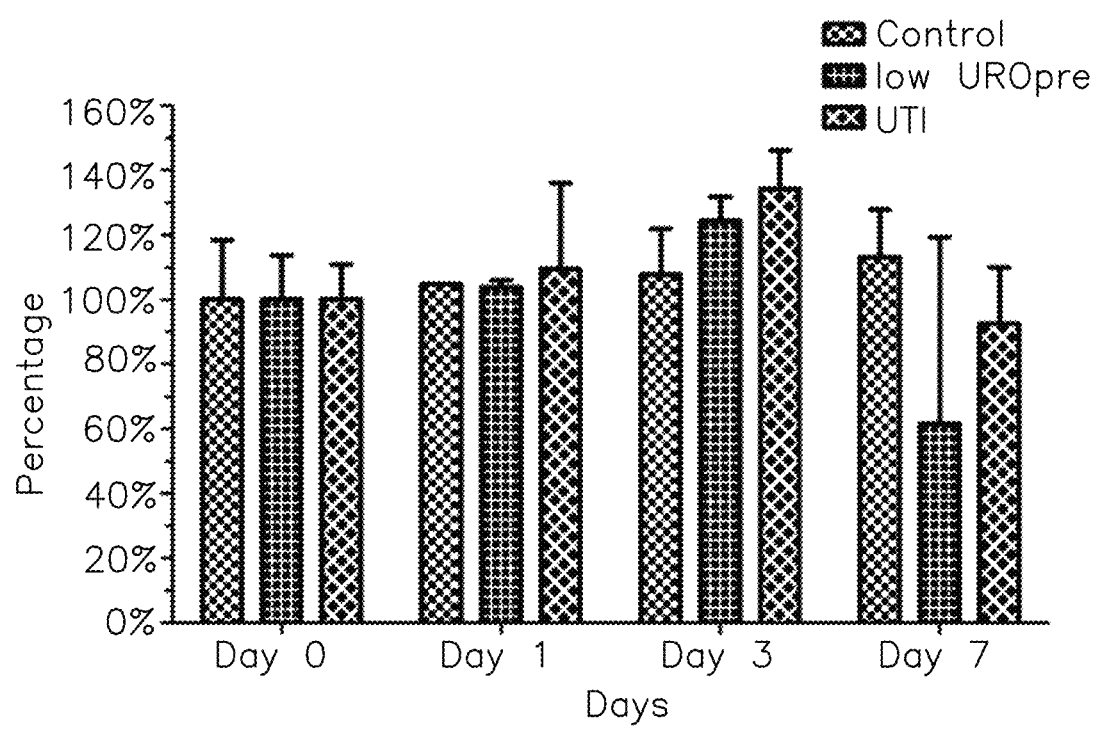
FIG. 11 is a bar chart comparing the peripheral WBC count percentages of the control group, the reduced PPS dosage group, and the UTI model group in the PPS oral dosage administration experiment in the rats, in accordance with an embodiment of the present disclosure.

Example 3: The Efficacy of Low-Dose PPS Oral Administration in Preventing Urinary Tract Infection in Rats The purpose of the current example is to investigate effects of a reduced dosage of PPS for preventing UTI in the rat URI model. The SD rats are randomized and grouped into a control group (N=7), an UTI model group (N=10), a normal PPS dosage group (N=10), and a reduced PPS dosage group (N=5). The UTI model group, the normal PPS dosage group, and the reduced PPS dosage group are infected with UPEC on Day 1. The method of infection and the amount of UPEC being injected to the rats of the current study are the same as the UPEC infection in Example 1. The normal PPS dosage group is orally administered with 30 mg/kg/day PPS per day from Day −14 to Day 0, and the reduced PPS dosage group is orally administered with 8.5 mg/kg/day PPS per day from Day −14 to Day 0, whereas the UTI model group does not receive PPS administration. The control group is not infected by the UPEC or treated by PPS. Urine samples and the blood samples of the rats are collected on Day 0, 3, and 7, using the same techniques and tools as described in Example 1. The collected urine samples are diluted 10, $10^2$, $10^3$, $10^4$, and $10^5$ folds, and the diluted urine samples are cultured on BSA plates and incubated for 12 hours at 37° C. UPEC colonies on the BSA plates are counted after the incubation. In FIGS. 10 and 11, the UTI model group is denoted as "UTI", the normal PPS dosage group is denoted as "UROpre", and the reduced PPS dosage group is denoted as "low UROpre".

FIG. 10 is a bar chart comparing the urine bacterial counts of the control group, the normal PPS dosage group, the reduced PPS dosage group, and the UTI model group, in accordance with an embodiment of the present disclosure. The urine bacterial counts in the low UROpre group are similar to the urine bacterial counts in the UROpre group, wherein the urine bacterial counts in both groups are lower than the UTI model group on Day 3.

FIG. 11 is a bar chart comparing the peripheral WBC count percentages of the control group, the reduced PPS dosage group, and the UTI model group, in accordance with an embodiment of the present disclosure. The WBC counts reflects a current urinary tract infection episode, the WBC count percentage can be a relative indicator comparing the WBC counts before the infection and after the infection. The WBC count percentages in FIG. 11 are used to examine the efficacy of the reduced PPS dosage in the rat UTI model. The WBC counts on Day 0 in the control group, the reduced PPS dosage group, and the UTI group are designated as 100% in FIG. 11. The WBC count percentages of the 3 groups are elevated on Day 1, reflecting more WBCs entering the peripheral blood after the infection. On Day 3, the WBC count percentage of the low UROpre group is about 120%, whereas the WBC count percentage of the UTI group is about 130%. This demonstrates the UPEC infection is effectively under control in the low UROPre group from Day 3. On Day 7, the WBC count percentage in the low UROpre group is about 60%, which is significantly lower than that of the UTI group.

To conclude, with less than ⅓ of the PPS dosage administered in Example 1, the 8.5 mg/kg/day orally-administered PPS dosage used in the current example is therapeutically effective in the rat UTI model. The 8.5 mg/kg/day PPS dosage has similar therapeutic effects with the 30 mg/kg/day PPS dosage.

The above examples have demonstrated the efficacy and the therapeutic effective dosage of orally administered PPS, in the rats or in the human subjects, in accordance with embodiments of the present disclosure. To control the UPEC infection, PPS needs to be continuously administered for 14 days in the rats before the UPEC infection.

The therapeutic effective dosage of PPS in the rats can be converted to an equivalent dosage in the human subjects, based on body weight and body surface areas. According to Nair, A. B. and Jacob S. (Nair, A. B., & Jacob, S. (2016). A simple practice guide for dose conversion between animals and human. Journal of basic and clinical pharmacy, 7(2), 27.), the therapeutic effective dosage of PPS for the human subjects can be converted to the dosages for the rats, after being divided by a conversion coefficient of 0.162, or that the dosage for the rats being multiplied by 0.162 to generate the dosage for the human subjects. See Table 2 below for a detailed dosage conversion table between the human subjects and the rats.

TABLE 2

Dose conversion between human and rat

| Total administered amount in the human subject (per day) | Reference body weight of the human subject | Dosage for the human subject (per kg per day) | Dosage for the rat (per kg per day) |
| --- | --- | --- | --- |
| 300 mg | 60 kg | 5 mg | ≒ 30.86 mg |
| 291.6 mg | | 4.86 mg | 30 mg |
| 200 mg | | ≒ 3.33 mg | ≒ 20.58 mg |
| 100 mg | | ≒ 1.67 mg | ≒ 10.29 mg |
| 85 mg | | ≒ 1.42 mg | ≒ 8.74 mg |
| 82.62 mg | | ≒ 1.38 mg | 8.5 mg |
| 75 mg | | ≒ 1.25 mg | ≒ 7.72 mg |
| 60 mg | | 1 mg | ≒ 6.17 mg |

According to Table 2 and one or more embodiments of the present disclosure, the therapeutic effective dosage of less than 5 mg/kg/day PPS demonstrates sufficient efficacy in preventing rUTI in the human subjects. In Example 2, the dosage of less than 5 mg/kg/day PPS, or the total administered amount of 300 mg PPS per day for the human subjects (with the reference weight of female human subjects being 60 kg), has been proven to be therapeutically effective. A reduced dosage of about 3.34 mg/kg/day PPS, or the total administered amount of 200 mg PPS per day for the remaining 8 weeks demonstrates that it is also therapeutically effective. Furthermore, Example 3 has demonstrated that, an even lower dosage of 8.5 mg/kg/day PPS for the rats, administered for 14 days, has similar efficacy with the dosage of 30 mg/kg/day PPS in preventing urinary tract infection. According to Table 2, 8.5 mg/kg/day PPS in the rats is equivalent to 1.38 mg/kg/day PPS in the human subjects, and 30 mg/kg/day PPS in the rats is equivalent to 4.86 mg/kg/day PPS in the human subjects. This suggests a dosing regimen of PPS with the dosage of 1.38 mg/kg/day should be also effective to prevent rUTI and minimize PPS adverse effects in the human subjects.

A reduced dosage of PPS implies a higher clinical compliance, because the patients would be taking fewer pills than that of the normal dosage, and increases the willingness of the patient to take PPS medication. Thus, a consistent and long-term dosing regimen for preventing rUTI would be possible for the patients with previous UTI episodes.

Previous descriptions are only embodiments of the present disclosure and are not intended to limit the scope of the present disclosure. Many variations and modifications according to the claims and specification of the disclosure are still within the scope of the claimed disclosure. In addition, each of the embodiments and claims does not have to achieve all the advantages or characteristics disclosed. Moreover, the abstract and the title only serve to facilitate searching patent documents and are not intended in any way to limit the scope of the claimed disclosure.

What is claimed is:

1. A method for preventing recurrent urinary tract infection (rUTI), comprising:
   in a human subject without showing lower urinary tract symptoms, orally administering a therapeutically effective dosage of pentosan polysulfate sodium (PPS), wherein the therapeutically effective dosage is 5-1 mg/kg/day.

2. The method for preventing recurrent urinary tract infection (rUTI) in the human subject according to claim 1, wherein the therapeutically effective dosage is 3.4-1.67 mg/kg/day.

3. The method for preventing recurrent urinary tract infection (rUTI) in the human subject according to claim 1, wherein the therapeutically effective dosage is 1.67-1 mg/kg/day.

4. The method for preventing recurrent urinary tract infection (rUTI) in the human subject according to claim 3, wherein the therapeutically effective dosage is 1.42-1.25 mg/kg/day.

5. The method for preventing recurrent urinary tract infection (rUTI) in the human subject according to claim 3, wherein the therapeutically effective dosage is 1.25-1 mg/kg/day.

* * * * *